United States Patent [19]
Perfetti

[11] Patent Number: 5,488,962
[45] Date of Patent: Feb. 6, 1996

[54] CHEWING GUM WHICH IS A SUBSTITUTE FOR TOBACCO SMOKE

[75] Inventor: Georgio Perfetti, Lainate, Italy

[73] Assignee: Perfetti, S.p.A., Milan, Italy

[21] Appl. No.: 348,768

[22] Filed: Dec. 2, 1994

Related U.S. Application Data

[63] Continuation of Ser. No. 44,476, Apr. 9, 1993, abandoned, which is a continuation-in-part of Ser. No. 718,473, Jun. 20, 1991, abandoned.

[30] Foreign Application Priority Data

Oct. 10, 1990 [IT] Italy ..................................... 21694/90

[51] Int. Cl.⁶ .................................................... A24B 15/00
[52] U.S. Cl. ............................. 131/270; 131/271; 424/48
[58] Field of Search .................................... 131/270, 271, 131/352; 424/48

[56] References Cited

U.S. PATENT DOCUMENTS 3,877,468  4/1975  Lichtneckert et al. .
4,971,079  11/1990  Talapin et al. ....................... 131/270 X Primary Examiner—Jennifer Bahr
Attorney, Agent, or Firm—Sughrue, Mion, Zinn, Macpeak & Seas

[57] ABSTRACT

Chewing gum which is a substitute for tobacco smoke, formed into three 3 g strips, characterized in that each strip contains not more than 25 wt % of a gum base and not more than 0.4 mg of nicotine dispersed in the gum base. The invention provides a nicotine-containing gum which simulates cigarette smoking (by providing a level of nicotine retention in the blood and saliva very similar in intensity and duration to that due to cigarette smoking), without accompanying problems with respect to unpleasant taste, poor chewing characteristics and undesirable side-effects.

4 Claims, 4 Drawing Sheets

CHEWING GUM WHICH IS A SUBSTITUTE FOR TOBACCO SMOKE

CROSS REFERENCE TO RELATED APPLICATIONS

This is a Continuation of application Ser. No. 8/044,476 filed Apr. 9, 1993, now abandoned, which in turn is a Continuation-In-Part of U.S. application Ser. No. 07/718,473 filed Jun. 20, 1991, now abandoned.

FIELD OF THE INVENTION

The present invention relates to chewing gum of the type which includes nicotine as a substitute for tobacco smoke.

BACKGROUND OF THE INVENTION

It is well known that among the many substitutes which have been proposed to reduce the need and/or craving to smoke, chewing gums including nicotine have been found to be quite successful. In fact, it has been established that assimilation of nicotine from a source other than tobacco can be of considerable help to a smoker who wishes to give up smoking.

In order to have the desired effect, prior art chewing gums of the type in question had to contain from 1 to 4 mg of nicotine per 3 g strip of gum. Furthermore, the prior art chewing gums had to retain the nicotine so as to release the nicotine slowly over not less than 10 minutes during chewing. This slow release was necessary because a more rapid assimilation of the required amount of nicotine could give rise to undesirable side-effects such as, for example, heart palpitations, tachycardia, migraine, irritation of the mouth or throat, etc. The lower limit of 1 mg of nicotine was established, also according to the prior art, because no medium was known which could usefully be incorporated in a chewing gum and could release such a small quantity of nicotine over a period as long as 10 minutes.

A chewing gum which satisfies the requirements of the prior art is described in Italian Patent No. 1,044,563 corresponding to U.S. Pat. No. 3,901,248.

This patent describes the preparation of chewing gum including a cation-exchange resin which is finely dispersed in the gum base and to which predetermined quantities of from 1 to 5 mg of nicotine are bound. Although, on the one hand, such a chewing gum achieves the predetermined object of slowly releasing the nicotine, on the other hand, this chewing gum disadvantageously is organoleptically less pleasant precisely because of the presence of the cation exchange resin. Namely, the cation-exchange resin gives the gum a particularly unpleasant taste.

Italian Patent No. 1,045,528 corresponding to U.S. Pat. No. 3,877,468 describes a chewing gum including not less than 40% by weight of a gum base in which the nicotine is dispersed in the form of a free base or a pharmacologically-acceptable addition salt of nicotine, or even as a complex including an adsorbent substance which binds nicotine or a salt thereof. In this case, the chewing gum also has the desired advantage that it releases the nicotine slowly but, because of the high percentage of its gum base content, it has the disadvantage that it does not afford soft or linear chewing. The term linear chewing is intended to define a characteristic of the consistency of the chewing gum as a result of which the effort required to chew the same is constant or almost constant over a period of time. It is well known that a gum base is generally a fairly stiff, solid substance which must be used in quite small percentages, generally not greater than 25% of the finished product by weight, so that it can be softened or plasticized by the sugary matrix and, in particular, by the flavoring ingredients of the chewing gum.

The otherwise recognized effectiveness of the nicotine gums of the prior art may be frustrated by their mainly organoleptic disadvantages which often constitute a psychological alibi or justification for the smoker's lack of will to persevere in his attempt to give up smoking.

SUMMARY OF THE INVENTION

A primary object of the present invention is to provide a chewing gum which includes nicotine as a smoke substitute and which overcomes the problems mentioned above with reference to the prior art, while being of real help to a smoker who intends to give up smoking.

This object and others which will become apparent from the description which follows are achieved by a chewing gum formed into 3 g strips, characterized in that each strip includes not more than 25% by weight of a gum base and not more than 0.4 mg of nicotine or a salt thereof dispersed in the gum base. In a preferred embodiment, the chewing gum of the invention does not contain a cation-exchange resin.

The smaller quantity of nicotine assimilated during the chewing of a strip of chewing gum according to the invention has shown a complete lack of side-effects of the type described with reference to the prior-art nicotine chewing gums. On the other hand, even when many strips of chewing gum according to the invention were chewed daily, it was surprisingly found that the smokers' response, meaning the levels of nicotine retention in the blood and the saliva of subjects selected for the tests, was very similar in intensity and duration to that due to cigarette smoking.

The gum of the invention was therefore found to be considerably more effective than gums of the prior art, which was completely unexpected in view of the palatability and taste of the gum.

Namely, the present invention provides a nicotine-containing gum which simulates cigarette smoking (by providing a level of nicotine retention in the blood and saliva very similar in intensity and duration to that due to cigarette smoking), without the accompanying problems of the prior art with respect to unpleasant taste (due to cation-exchange resin), poor chewing characteristics and undesirable side-effects.

BRIEF DESCRIPTION OF THE DRAWINGS

The characteristics and advantages of the invention will become apparent from the following description given with reference to the appended drawings, in which.

DETAILED DESCRIPTION OF THE INVENTION

The chewing gum of the present invention has a gum base content of not more than 25 wt. %, preferably a gum base content of from 18–25 wt. %, and more preferably a gum base content of from 20–25 wt. %. The chewing gum of the invention contains not more than 0.4 mg of nicotine per 3 g strip, and preferably contains from 0.3–0.4 mg of nicotine per 3 g strip.

In a preferred embodiment, the chewing gum of the invention does not contain a cation-exchange resin.

For details regarding the gum base and nicotine for use in the present invention, reference may be made to U.S. Pat. No. 3,877,468 to Lichtneckert et al and Italian Patent Nos. 1,044,563 and 1,045,528 corresponding to U.S. Pat. Nos. 3,901,248 and 3,877,468, respectively.

Figure 1:
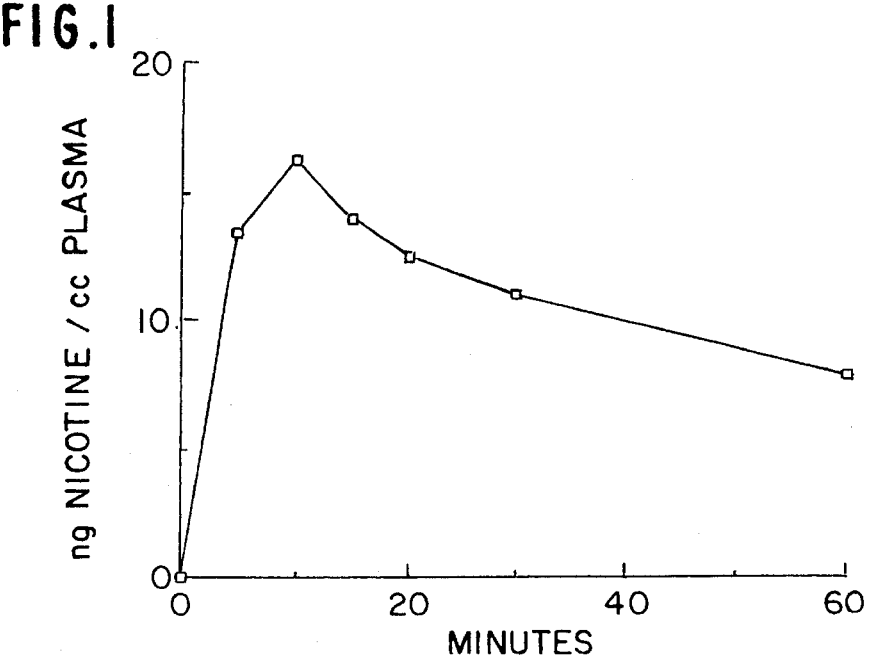
FIG. 1 shows a curve typical of nicotinaemia due to cigarette smoking.

FIG. 1 shows the time course of the plasma nicotine levels resulting from cigarette smoking. As clearly shown in the graph, the peak level is obtained after ten (10) minutes.

Figure 2:
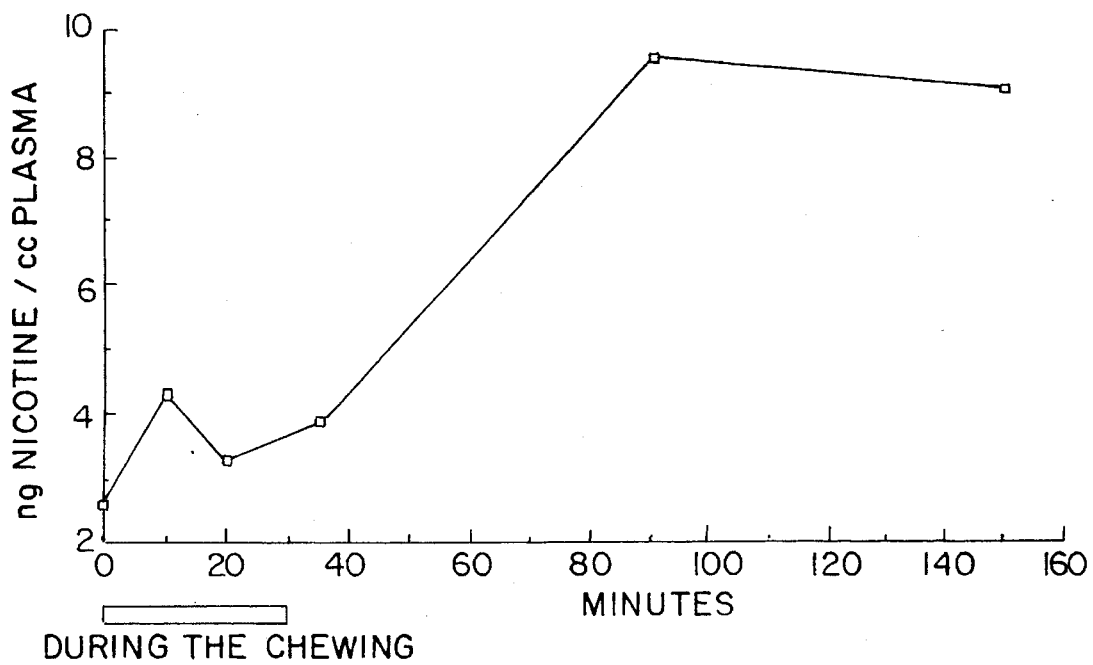
FIGS. 2 and 3 are graphs relating to the nicotinaemia levels reached after the administration of one strip of chewing gum of the prior art and four strips of chewing gum simultaneously chewed according to the invention, respectively.

FIG. 2 shows the time course of the plasma nicotine levels resulting from the chewing of a single strip of NICORETTE chewing gum which has two mg of nicotine. The curve in FIG. 2 has a completely different shape from that of the previous Figure showing the results from cigarette smoking. The plasma peak level in FIG. 2 is obtained only 90 minutes after start of chewing the gum.

Figure 3:
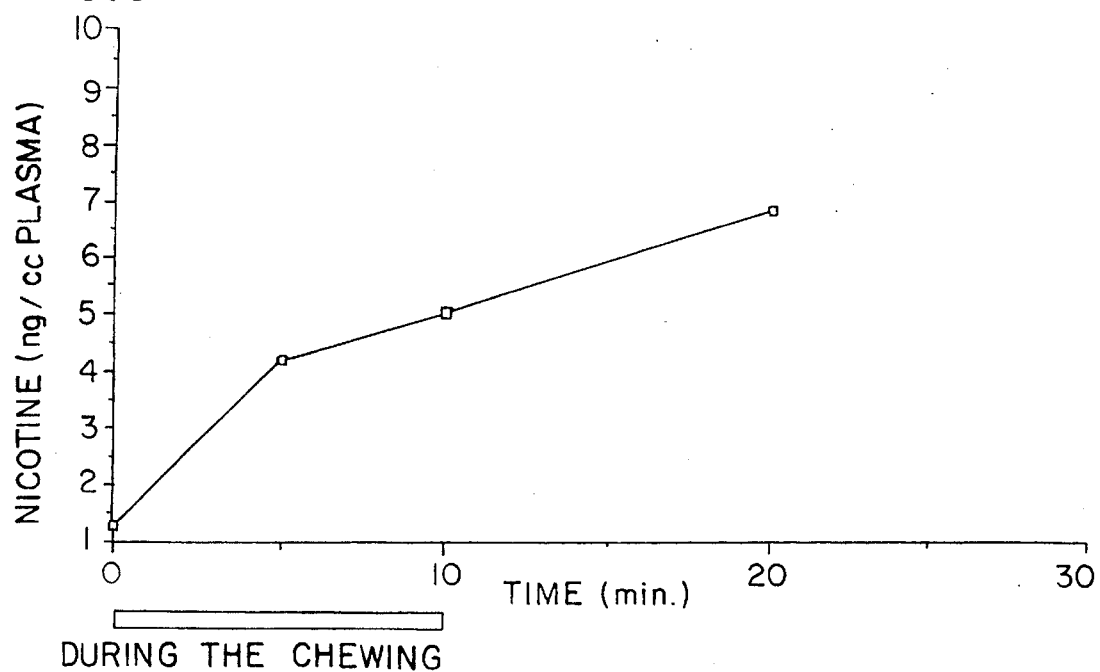

FIG. 3 shows the time course of the plasma nicotine levels resulting from simultaneously chewing four strips of chewing gum according to the present invention, each having 0.4 mg of nicotine. The curve indicates the presence of a very sustained absorption of nicotine which reaches a level of 4 mg/ml plasma after 10 minutes and a peak value which is obtained after 20 minutes.

Figure 4:
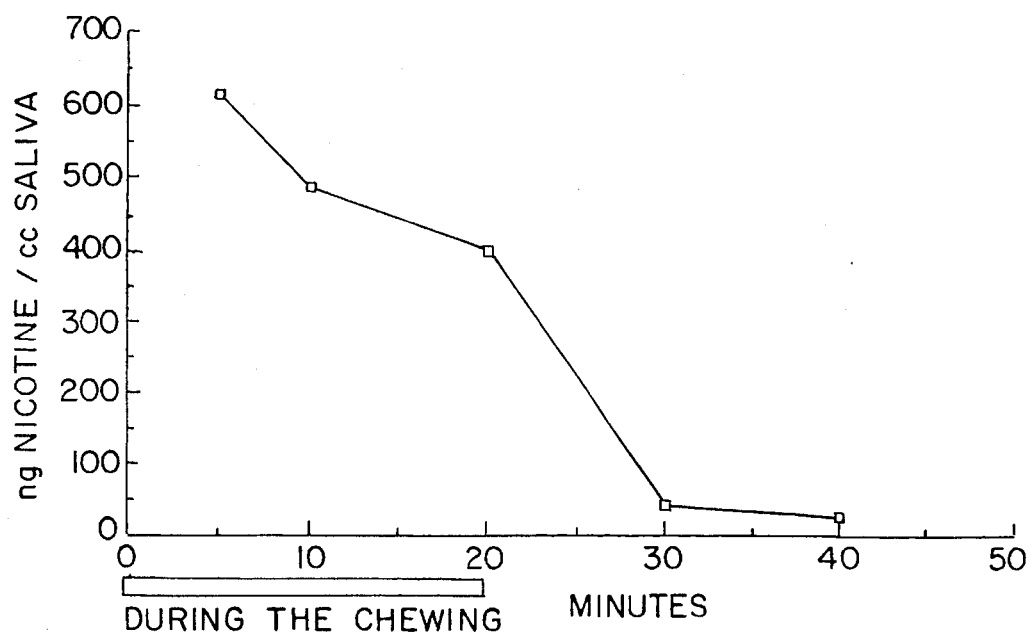
FIG. 4 shows a graph of the nicotine levels in the saliva during and after the chewing of a single strip of chewing gum according to the invention.

FIG. 4 shows the time course of the disappearance of nicotine from the saliva while chewing a single strip containing 0.4 mg of nicotine. The nicotine is rapidly released in the mouth during chewing and after 30 minutes, the amount of nicotine found in the mouth is negligible. Since nicotine probably enters the body through the sublingual absorption, the possibility of rapidly releasing small amounts of nicotine in the mouth mimics cigarette smoking as closely as possible. This can be observed by comparing plasma nicotine levels 10 minutes after cigarette smoking or chewing four (4) strips of 0.4 mg each of chewing gum, that is, 16 ng/ml vs. 4.8 ng/ml. These two values are of the same order of magnitude and indicate a comparable exposure to nicotine.

Figure 5:
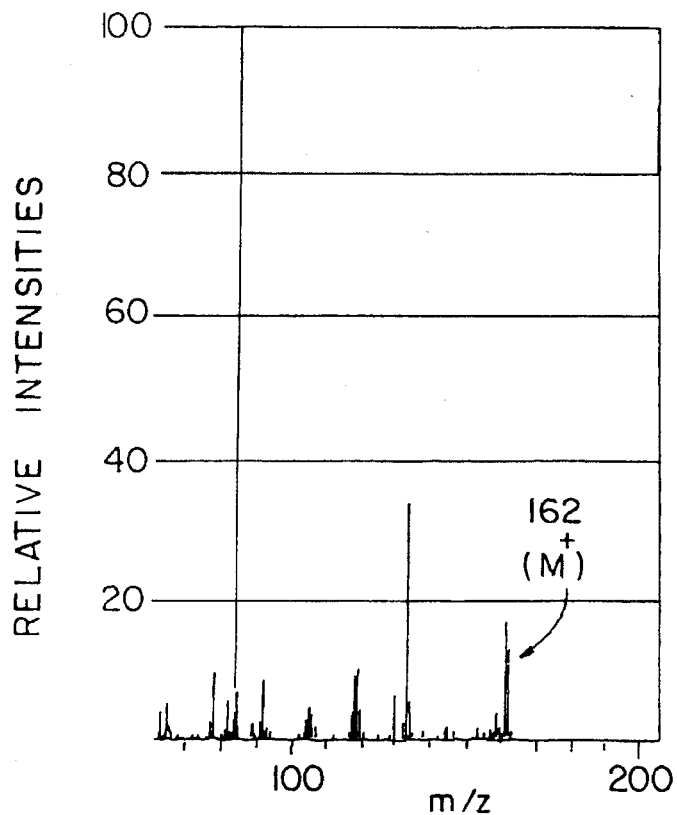
FIGS. 5 and 6 show the mass spectra of nicotine and of nicotine marked with deuterium, respectively.

FIG. 5 shows the mass spectra of nicotine wherein the molecular radical cation can be seen at mass/charge (m/z) 162. The base peak, that is, the most intense ion, appears at m/z 84, corresponding to the cleavage with subsequent loss of the pyridyl moiety. This fragmentation is typical for nicotine and well described in the literature (JACS 8713, 2926 (1965)).

Figure 6:
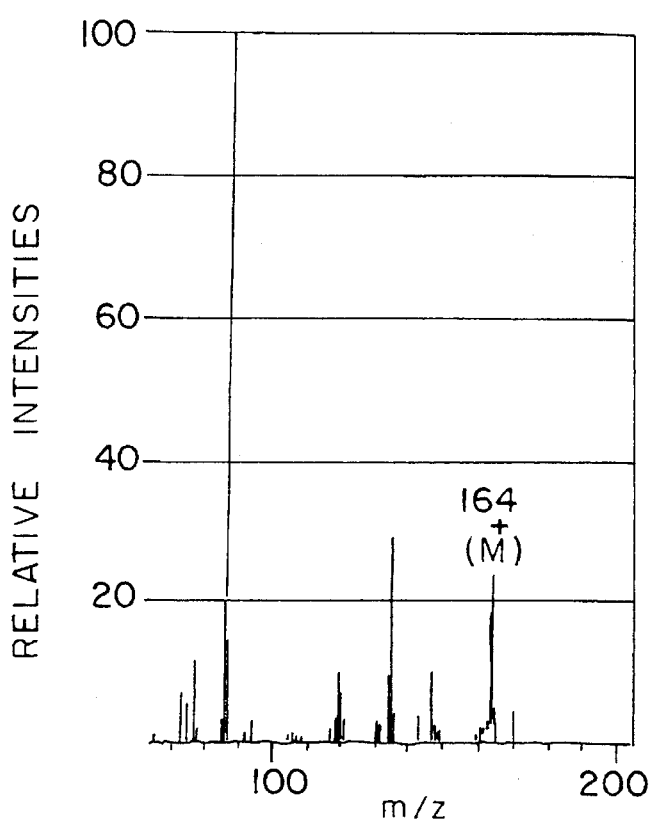

FIG. 6 is the mass spectra of deuterated nicotine. This molecule, compared to nicotine, has the hydrogens in position 5 and 5' substituted with deuterium atoms. This does not change its chemical properties, but only its molecular weight. Since mass spectrometers separate masses very well, it is therefore possible to add it in a known amount to the plasma sample and measure relative concentrations of non-deuterated nicotine vs. deuterated nicotine. Precision and accuracy of the analysis are better than conventional analysis. In this spectra, the molecular ion is seen at m/z 164, shifted of two mass units compared to that of nicotine. This shift is due to the different weight of the deuterium atoms compared to hydrogen atoms. The base peak appears again at m/z 84 since with the loss of the pyridyl moiety, the deuterium atoms are also lost.

Figure 7:
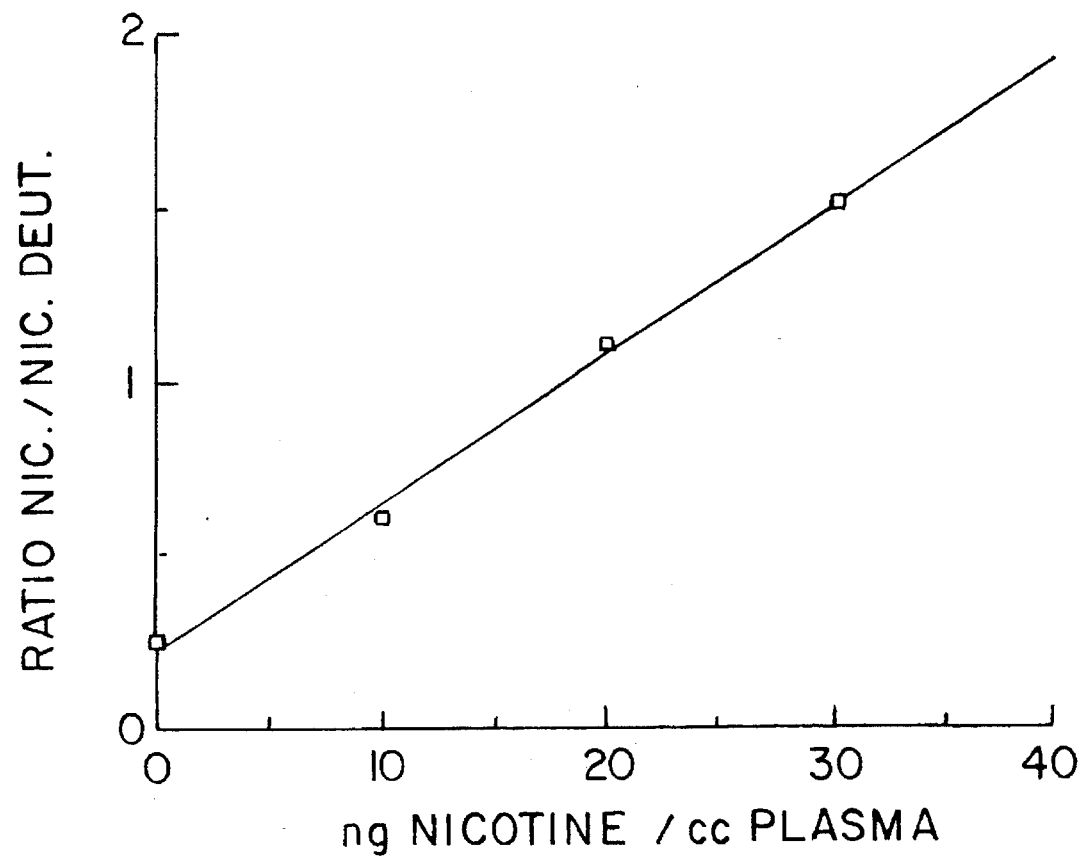
FIG. 7 shows a calibration line for nicotine in plasma.

FIG. 7 is a graph showing the calibration line for nicotine in plasma. Nicotine concentration is measured relative to that of deuterated nicotine. Deuterated nicotine is added to samples as internal standards in known concentration. Measurements are performed by monitoring the intensity of the ion current produced by the molecular ions of nicotine and deuterated nicotine (m/z 162 and 164, respectively). It can be seen that the different amounts of nicotine give different ratios of nicotine/deuterated nicotine, and that this follows a linear trend allowing quantitative analysis to be done.

For testing, 3 g strips of chewing gum according to the invention were prepared.

Each Strip had the following composition:

|  | by weight |
| --- | --- |
| gum base | 25.0 |
| glucose syrup | 18.0% |
| sucrose | 55.5% |
| glycerol | 0.8% |
| natural flavoring (spearmint oil) | 0.7% |
| nicotine | 14.2 mg per 100 g |

The biological availability of the nicotine in a 3 g strip of chewing gum according to the invention was evaluated by comparison with that in cigarette smoke and in a 3 g strip of a prior-art nicotine gum sold under the name of NICORETTE and including 60% by weight of a gum base and 2 mg of nicotine dispersed in the base.

EXPERIMENTAL TESTS a) Nicotine levels in saliva

A strip of chewing gum according to the invention containing 0.4 mg of nicotine was chewed by a volunteer who had abstained from smoking for 10 hours. The gum was chewed for 20 minutes.

Saliva samples were taken at the following times during chewing: 5, 10 and 20 minutes. Samples were also taken 10 and 20 minutes after chewing (30 and 40 minutes after chewing started, respectively).

b) The kinetics of the nicotine after four pieces of gum according to the invention had been simultaneously chewed Kinetics tests were carried out on a volunteer in order to follow the progress of his nicotine retention after four pieces of chewing gum with a total nicotine content of 1.6 mg had been administered. It was elected to use four strips of chewing gum in order to achieve nicotinaemia levels high enough to enable measurement and a direct comparison with NICORETTE (2 mg of nicotine).

The volunteer was a non-smoker and chewed the chewing gum for 10 minutes. Samples were taken at the start and 5, 10 and 20 minutes after chewing started.

c) Nicotine retention levels after the administration of one strip of NICORETTE

Kinetics tests were carried out on a volunteer in order to follow the progress of nicotine retention after a single strip of NICORETTE (2 mg of nicotine) had been administered. The volunteer was a smoker. The experiment was carried out after 10 hours abstinence from smoking.

The gum was chewed for 20 minutes and samples were taken at the start and after 10, 20, 35, 90 and 150 minutes.

| Characteristics of the subjects | |
|---|---|
| age | 20–28 years |
| sex | 2 male smokers and 1 female non-smoker |
| weight | 50–70 Kg |
| No. of cigarettes habitually smoked | 15–20 per day of the following brands: Lucky Strike, MS |

The reagents used were nicotine and 98% deuterated lithium aluminum hydride from Janssen Chimica, 2304 Beerse, Belgium; cotinine from Sigma (PO Box 14508, St. Louis, Mo., U.S.A.). The solvents, were D-6100 from Merck, Darmstadt, F. R. of Germany.

Instrumentation

A VG TS-250 mass spectrometer with an HP 5890 gas chromatograph was used. The ionization was effected by electron bombardment.

Synthesis of denatured nicotine

Nicotine marked with deuterium was prepared as an internal standard and was synthesized by us by the method of Duffield, Budzikiewics and Djerassi (1965). This method consists of the reduction of cotinine to nicotine-5,5-d2 by deuterated lithium aluminum hydride. FIG. 5 shows the mass spectrum of nicotine and FIG. 6 shows that of nicotine marked at position -5,5-d2.

The mass-to-charge values ($m^+/z$) are shown on the abscissae and their relative intensities are shown on the ordinates as percentages of the most abundant ions.

The extraction and measurement of the nicotine from plasma and saliva

The analytical method of Feyerabend and Russel (1978) was used to extract the nicotine from both the plasma and the saliva.

It should be stressed that the nicotine extracted was measured by a method which can achieve the sensitivity and specificity necessary to evaluate even small traces of nicotine in the plasma. As stated below, this method is based on the use of gas chromatography-mass spectrometry.

NaOH (2 ml, 5N) was added to a 1 ml sample (plasma or saliva) after the addition of the internal standard, and the mixture was extracted with ethyl ether (1 ml) and stirred in a vortex for two periods each of 2 minutes. HCl (1 ml, 1N) was added to the supernatant liquid which was then stirred in a vortex for an additional 2 minutes. After the organic phase had been removed, 0.5 ml of NaOH (5N) was added to the residue and the mixture extracted with n-hexane (0.5 ml) and stirred in a vortex for 2 minutes.

The extract was concentrated gently to about 50 µl under a flow of nitrogen. The product was ready for instrumental analysis by gas chromatography-mass spectrometry.

The quantitative determination was effected with the use of calibration lines obtained by the recovery of known quantities of nicotine from saliva or plasma matrices from non-smokers. FIG. 7 shows the calibration line for nicotine and plasma.

The gas chromatography-mass spectrometry was carried out under the following conditions:

| | |
|---|---|
| column | WCOT Cp WAX 57 CB length: 11 m int. diameter: 0.22 mm |
| pressure | 30 kPa |
| injector | On column |
| program | 60° C. for 1 minutes - 240° C. |
| ionization potential | 20 eV |
| specific ions | nicotine $m^+/z$ 162 nicotine d2 $m^+/z$ 164 |

FIGS. 2 and 3 show respectively the nicotine retention levels obtained after the administration of a single strip of NICORETTE chewing gum (2 mg of nicotine) and of four pieces of chewing gum simultaneously chewed each containing 0.4 mg of nicotine.

FIG. 4 gives the nicotine levels in the saliva during and after the chewing of a strip of chewing gum with 0.4 mg.

The tests described above enabled the following conclusions to be drawn.

a) The nicotine levels in the saliva during and after the chewing of a 0.4 mg strip of gum indicate that the nicotine is released quickly during chewing. The nicotine levels in the saliva decrease sharply as soon as chewing stops.

b) The levels of nicotine in the blood during the chewing of four pieces of gum rise rapidly and remain fairly constant throughout the measurement period. The levels reached are comparable with those reached with NICORETTE (2 mg), but the maximum levels are reached more quickly.

c) A comparison of the nicotine retention levels reached after gum according to the invention has been chewed and after cigarettes have been smoked shows that, except for the very first minutes, when cigarette smoke produces the highest values, the curves of the nicotine retention levels are quite comparable. Comparable levels are reached with Nicorette 2 mg, but absorption is substantially quicker with the chewing gum of the invention.

Surprisingly, Applicant ascertained during his studies that:

(a) The inventive recipe allows for total bioavailability of the nicotine incorporated in the gum. In fact, the measurement data of nicotine in the volunteers' blood and saliva were unmistakable evidence of this.

(b) The kinetics of nicotine in the volunteers' plasma during and after chewing the inventive gum was quite similar to that observed during and after smoking a cigarette (see the data as presented in FIGS. 2 and 3).

Particularly interesting is the nicotine peak observed immediately after chewing the inventive gum, which correlates well to the effects of smoking a cigarette. In fact, the initial "relaxing" effect of smoking is ascribed to this nicotine peak, which corresponds to a sudden increase of nicotine levels in the plasma and to consequent vaso-dilatation. The plasma kinetics of nicotine during and after the chewing of a NICORETTE gum is completely different, because the plasma peak appears later and elimination from the bloodstream takes much longer.

The inventive chewing gum provides results which are markedly different from those of the prior art with respect to nicotine retention in blood plasma (characterized in terms of intensity and duration). More particularly, the inventive gum better simulates cigarette smoking (i.e., rapid absorption), whereas the prior art gums are designed to slowly release nicotine (to thereby prevent the undesirable side-effects).

Namely, the above noted effects of the present invention are achieved by (1) limiting the gum base content to not more than 25% by weight (to thereby rapidly release the nicotine dispersed therein), and by (2) limiting the nicotine content to not more than 0.4 mg per strip (to thereby overcome the side-effects of the type described by reference to the prior art nicotine chewing gums).

Thus, the differences between the inventive gum and that of the prior art gums are the gum base content and nicotine content, which characteristics unexpectedly provide the effects of the invention (i.e, good simulation of cigarette smoking).

Furthermore, in the prior art chewing gums, the quantity of gum base is much greater than 25% and typically more than 40%, and therefore does not provide for linear chewing. The reasons are as follows:

- an effective chewing gum, as a substitute of smoke according to prior art, must contain from 1 to 4 mg of nicotine;
- it is necessary to employ a cation-exchange resin to incorporate into the gum this high content of nicotine;
- the strips, in order to offer good chewing characteristics, must contain about 25% or less of gum base;
- the cation-exchange resins make the strips brittle;
- to avoid this inconvenience, it is necessary to increase the content of gum base to 40% and higher;
- in doing so, the strips are no longer brittle, but cannot be easily chewed.

The present Applicant achieves a result different from the prior art chewing gums (i.e., rapid release of nicotine to thereby better simulate cigarette smoking), by limiting the gum base content to not more than 25%. Moreover, the nicotine content of the inventive gum is limited to not more than 0.4 mg per strip, to thereby overcome the undesirable side effects of rapidly assimilating a large quantity of nicotine.

Namely, according to the present invention, a low nicotine content (i.e., 0.4 mg per strip) is surprisingly effective as a substitute for cigarette smoke. Applicant's discovery is contrary to what one of ordinary skill in the art would expect. Furthermore, by employing a low nicotine content, the use of cation-exchange resins is avoided.

It should further be apparent to those skilled in the art that various changes in form and detail of the invention as shown and described above may be made. It is intended that such changes be included in the spirit and scope of the claims appended hereto.

What is claimed is:

1. Chewing gum which is a substitute for tobacco smoke, formed into 3 g strips, characterized in that each strip contains not more than 25 wt. % of a gum base and from 0.3–0.4 mg of nicotine dispersed in the gum base.

2. The chewing gum of claim 1, wherein each strip contains from 18–25 wt. % of a gum base.

3. The chewing gum of claim 1, wherein each strip contains from 20–25 wt. % of a gum base.

4. The chewing gum of claim 1, which does not contain a cation-exchange resin.

\* \* \* \* \*